(12) United States Patent
Besse

(10) Patent No.: US 7,682,629 B1
(45) Date of Patent: Mar. 23, 2010

(54) FLOATING PHARMACEUTICAL COMPOSITION COMPRISING AN ACTIVE PHASE AND A NON-ACTIVE PHASE

(75) Inventor: Jerome Besse, Listrac Medoc (FR)

(73) Assignee: Galenix Developpement (FR)

( * ) Notice: Subject to any disclaimer, the term of this patent is extended or adjusted under 35 U.S.C. 154(b) by 206 days.

(21) Appl. No.: 10/048,459

(22) PCT Filed: Aug. 2, 2000

(86) PCT No.: PCT/FR00/02223

§ 371 (c)(1),
(2), (4) Date: May 14, 2002

(87) PCT Pub. No.: WO01/10417

PCT Pub. Date: Feb. 15, 2001

(30) Foreign Application Priority Data

Aug. 6, 1999 (FR) .................................. 99 10285

(51) Int. Cl.
*A61K 9/20* (2006.01)
*A61K 9/22* (2006.01)
*A61K 9/24* (2006.01)

(52) U.S. Cl. ........................ 424/473; 424/464; 424/465; 424/468; 424/471; 424/472

(58) Field of Classification Search .................. 424/464, 424/466, 468, 465, 474
See application file for complete search history.

(56) References Cited

U.S. PATENT DOCUMENTS

| 4,167,558 | A | * | 9/1979 | Sheth et al. ................. 424/465 |
| 5,626,876 | A | * | 5/1997 | M uller et al. .............. 424/484 |
| 5,780,057 | A | * | 7/1998 | Conte et al. ................. 424/468 |
| 5,783,212 | A | * | 7/1998 | Fassihi et al. ............... 424/472 |
| 6,197,328 | B1 | * | 3/2001 | Yanagawa ................... 424/434 |

FOREIGN PATENT DOCUMENTS

| EP | 0 235 718 A2 | 9/1987 |
| EP | 0 667 151 A1 | 8/1995 |
| EP | 0 669 129 A2 | 8/1995 |
| EP | 0 795 324 A | 9/1997 |

OTHER PUBLICATIONS

Remington's Pharmaceutical Sciences, Eighteenth Edition, 1990, pp. 1669-1670.*

* cited by examiner

*Primary Examiner*—S. Tran
(74) *Attorney, Agent, or Firm*—Arent Fox LLP

(57) ABSTRACT

The invention concerns a floating pharmaceutical composition consisting of at least a first phase comprising at least a high dose active principle combined with one or several carriers and at least a second phase comprising at least a gas-generating system. The invention also concerns tablets comprising such a pharmaceutical composition and a method for preparing such tablets.

18 Claims, 2 Drawing Sheets

Figure 1:
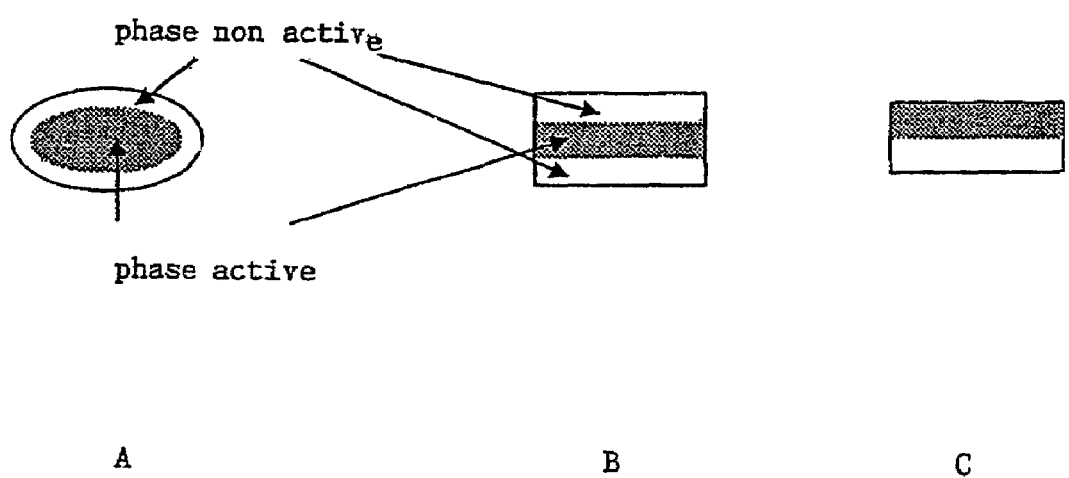

FLOATING PHARMACEUTICAL COMPOSITION COMPRISING AN ACTIVE PHASE AND A NON-ACTIVE PHASE

CROSS-REFERENCE TO RELATED APPLICATION

This application is a National Stage entry of International Application No. PCT/FR00/02223, filed Aug. 2, 2000, the entire specification claims and drawings of which are incorporated herewith by reference.

The present invention relates to a floating pharmaceutical composition constituted by at least a first phase comprising at least one very highly dosed active ingredient in combination with one or more excipients and at least one second phase comprising at least one gas-generating system.

The invention also relates to tablets containing such a pharmaceutical composition as well as to a process for the preparation of such tablets.

Various pharmaceutical compositions formulated in the form of floating tablets are known in the prior art.

For example, floating tablets have been obtained by acting on the density of the total composition, for example by varying the weight ratios between different polymer excipients such as the carboxymethylcellulose, ethylcellulose, cross-linked povidone or also chitosan, a compound well-known for its low density and for its muco-adhesive properties.

Another technical solution consisted of using, among the excipients, a porous mineral material such as calcium silicate in which air is imprisoned in the pores, the tablets being then coated with a polymer such as hydroxypropylcellulose or also ethylcellulose designed to retain the air within the porous mineral matrix.

Recourse was also had in the prior art to gelatine capsules filled with an inert gas or also filled with a substance containing bubbles of inert gas.

Another technical solution consisted of making use of hollow microspheres or polycarbonate resin filled with the active ingredient or also hollow microspheres containing the active ingredient in the presence of Eudragit-S, which are perfect spheres 500 to 1000 µm in diameter capable of floating for more than twelve hours in an acid medium in a 0.02% Tween-20 solution.

Another strategy consisted of obtaining a diminution of the density of the tablet at the time of use by incorporating in the pharmaceutical composition compounds capable of releasing a gas which remains, at least in part, imprisoned within this tablet and which will thus enable it to float on the surface of the gastric juice in the stomach.

The application PCT No. WO 98/47.506 describes a pharmaceutical composition designed to reside in the stomach and containing an active ingredient of the benzamide family in combination with a hydrophilic polymer or a porous mineral matrix and a carbon dioxide generating system. Such a pharmaceutical composition may be suitable for low doses of active ingredient, in particular when the dose of active ingredient in the tablet does not exceed 500 mg, as is usually the case for the benzamides. However, a modification of the dissolution profile of the active ingredient, compared with conventional pharmaceutical compositions not containing a gas-generating system, was observed for such compositions.

Furthermore, the fact that the gas-generating system and the active ingredient are in the form of an intimate mixture is such as to promote the interactions between the active ingredient and the other ingredients of the pharmaceutical composition, and this may lead to an at least partial chemical deterioration of the active ingredient and, consequently, to a significant diminution of the therapeutic efficacy of the composition as well as to problems of long-term storage.

ICHIKAWA et al. (1991, Journal of Pharmaceutical Sciences, vol.80, No.11, pages 1062-1066) have described a floating tablet constituted of a core containing a sustained-released pharmaceutical composition coated with a first layer comprising an effervescent couple, this first layer being itself coated with a polymer film capable of retaining a gas. Water or gastric juice penetrates through the external polymer film and enters into contact with the effervescent couple which then generates carbon dioxide. On being released within the tablet, the carbon dioxide will swell the tablet in the form of a "micro-balloon" capable of floating in the stomach. Such a tablet has the disadvantage of being difficult to produce industrially and is also expensive to manufacture. Furthermore, the filming of the effervescent couple layer by the polymer requires the use of solvents other than water, such as ethanol, dichloromethane or even acetone in order to prevent the effervescent couple from reacting at the time of manufacture.

In addition to the cost, the use of organic solvents poses the problem of their removal in the final stages of manufacture of the tablet, in a manner complying with the growing administrative constraints imposed prior to obtaining a marketing authorization for a pharmaceutical speciality.

The present invention overcomes the numerous disadvantages identified above concerning the floating compositions of the prior art and provides a novel pharmaceutical composition comprising at least one active phase and one inactive phase.

Thus, a first objective of the invention consists of a floating pharmaceutical composition constituted by at least:
  a) a first phase, termed active phase, comprising at least one active ingredient in combination with one or more excipients;
  b) a second phase, termed inactive phase, comprising at least one gas-generating system and at least one hydrophilic polymer or a porous mineral compound, the active phase comprising a quantity of active ingredient(s) constituting at least 80%, preferably at least 85% and very preferably at least 90% by weight of the active phase.

In accordance with a first feature, the active phase and the inactive phase have a common contact surface.

In accordance with a second feature, the active phase and the inactive phase are separated by a polymer layer.

In all cases, the active phase and the inactive phase are comprised in a single structure, for example, that of a tablet.

In a preferred embodiment the inactive phase is in direct contact with the external medium, for example gastric juice.

More precisely, in the case in which the pharmaceutical composition is formulated in the form of tablets, the active phase and the inactive phase are cemented together by compression according to procedures well-known to the one skilled in the art.

The nature of the inactive phase of the pharmaceutical composition according to the invention must be such that it makes possible the retention of the gas bubbles produced by the gas-generating system included in this latter for a sufficient time to permit the flotation of said pharmaceutical composition at the air/liquid interface, during transit through the gastro-intestinal tract.

That is why the second inactive phase may be composed either of a micro-network of hydrophilic polymer(s) or also of a porous mineral compound.

The gas-generating system is required to lower the high density of the pharmaceutical composition of the invention, this high density resulting from the high proportion of active ingredient(s) in the active phase of the composition.

Furthermore, the gas-generating system makes possible the rapid release of the gas, as soon as this system is placed in contact with the gastric or post-gastric aqueous medium, rapidly causing a decrease in the density of the pharmaceutical composition with a reaction rate much higher than that which would be observed with swellable polymers. The use of swellable polymers thus does not allow the technical problem of the invention to be resolved, because their swelling rate is not sufficient and would not enable the density of a pharmaceutical composition highly dosed with active ingredient(s) of the invention to be reduced sufficiently.

In addition, in a preferred embodiment, at least one of the surfaces of the inactive phase is directly in contact with the external medium. That means that the inactive phase is not coated with a film preventing any contact with the external medium.

In accordance with a first embodiment, the hydrophilic polymer of the inactive phase is selected from polysaccharide substances, related substances and protein substances.

Advantageously, the polysaccharide substances and the related substances are selected from the galactomannans and their derivatives, starch and its derivatives, gum arabic, tragacanth gum, the pectins and their derivatives, the alginate, cellulose and its derivatives, the high molecular weight dextrans or also xanthan and its derivatives.

These different substances include several commercial products that may be used such as, for example, METOLOSE® 90 SH 4000 SR (hypromellose or KLUCEL® HXF (hydroxypropylcellulose).

Preferably, the protein substances are selected from gelatine and its purified derivatives.

In accordance with another feature, the polymer used in the inactive phase is selected from the poloxamers, the high molecular weight polyethyleneglycols (higher than 6000 kDa) or also the polymers of the acrylic or methacrylic acids and their derivatives.

Preferably, the polymer or the mixture of polymers constituting the inactive phase forms a "gel" upon contact with an aqueous medium. There is a progressive hydration of the polymer particles with slight swelling of these latter, which then dissolve to form a "gel". The gel swells owing to the displacement of water from the aqueous medium into the inactive phase of the tablet.

In accordance also with another embodiment of the inactive phase of a pharmaceutical composition according to the invention, this inactive phase comprises a porous mineral compound selected from the silicas and their derivatives.

Advantageously, a calcium silicate or calcium fluoride-based matrix is used.

The inactive phase of the pharmaceutical composition according to the invention comprises in addition an agent designed to lower the density of the latter at the time of its administration to man or animals, this agent being constituted by a gas-generating system, such as a carbon dioxide generating system.

A carbon dioxide generating system preferably used within the inactive phase of a pharmaceutical composition according to the invention comprises an alkali or alkaline earth metal carbonate or also an alkali metal bicarbonate.

Calcium carbonate will be preferred as alkali metal carbonate.

Advantageously, the alkali metal bicarbonate is sodium bicarbonate or potassium bicarbonate.

A carbon dioxide generating system of a type defined above only produces carbon dioxide when it is in contact with an aqueous acid medium such as the gastric juice present in the stomach cavity. It is a so-called "pH dependent" carbon dioxide generating system.

In accordance with another embodiment, the inactive phase of the pharmaceutical composition according to the invention may contain a gas generating, in particular carbon dioxide generating, system called "pH independent".

In this particular embodiment, a carbon dioxide generating system comprises, as an intimate mixture, an alkali or alkaline earth metal carbonate or also an alkali metal bicarbonate such as defined above, in combination with an acid selected from the mono- and poly-carboxylic acids or also a partial salt of a polycarboxylic acid. Such a mixture is commonly called an effervescent couple.

By partial salt of a carboxylic acid is meant according to the invention a polycarboxylic compound in which only a portion of the carboxylic acid functions of the acid compound is combined with cations.

As examples of carboxylic acids, mention may be made of citric acid, tartaric acid and their partial salts such as monosodium and/or disodium citrate.

In the case where a pH independent carbon dioxide generating system is used, recourse will advantageously be had to a mixture in which the ratio between the alkali or alkaline earth metal carbonate or the alkali metal bicarbonate, on the one hand, and the mono- or polycarboxylic acid, in the salt or non-salt form, on the other, is approximately stoichiometric, in accordance with the conventional practices well-known to the one skilled in the art.

In accordance with another feature, the hydrophilic polymer or the porous mineral compound defined above in the inactive phase comprises from 10 to 70% by weight of said phase.

In accordance with a preferred embodiment, the gas-generating system, whether is be pH dependent or pH independent, in the inactive phase comprises from 5 to 60% by weight of said phase.

As already mentioned previously, the active phase of the floating pharmaceutical composition according to the invention comprises at least one active ingredient in combination with one or more excipients.

The constitution of this active phase may be of any kind known to the specialist. In fact, it has been shown that the dissolution profile of the active phase within a floating pharmaceutical composition according to the invention, i.e. in combination with the inactive phase, was not significantly changed, compared with the dilution profile observed for the active phase alone.

In particular, the active phase may contain a single active ingredient or, on the contrary, several active ingredients in combination, the active ingredient(s) being of any kind.

However, the particular flotation properties of the pharmaceutical composition according to the invention make it particularly suited to the use of active ingredients having a low or irregular bioavailability, due for example to low dissolution.

In fact, such active ingredients when they are included in conventional, non-floating compositions are released during a limited time in the stomach cavity, then are conveyed rapidly to the intestinal tract where the release of said active ingredient continues. Thus, in the case of active ingredients whose target sites are localized in the stomach or in the upper part of the small intestine, conventional pharmaceutical compositions do not allow adequate bioavailability of the active ingredient to saturate the sites, so as to permit optimal therapeutic action.

It is generally observed that a conventional tablet only resides in the stomach cavity for a time varying from 1 to 3 minutes, after which this tablet transits through the pylorus and then passes into the small intestine and is conveyed throughout the length of the intestinal tract to the colon.

In contrast, a tablet according to the invention floats on the gastric juice in the stomach.

It has been shown in vitro that the tablets constituted by a pharmaceutical composition according to the invention were capable of floating after about 30 seconds of contact following their immersion in an aqueous acid medium and were in addition capable of floating for about 10 to 20 hours.

This results in the active ingredient contained in the active phase being biologically accessible to the target sites for a prolonged time, on the one hand, and in that the totality of the dose of active ingredient initially contained in the active phase can have access to these target sites, on the other.

Advantageously, a pharmaceutical composition according to the invention comprises one or more active ingredients with a local action absorption window In fact, as a result of its flotation, a tablet of a pharmaceutical composition according to the invention permits the release of the active ingredient(s) contained in the active phase upstream or at the target sites of these latter for a long period of time and the saturation of the target sites for a much longer time than the non-floating tablets of the prior art. Particular advantage is taken of these flotation characteristics of a tablet of the invention when bimodal release is desired. The localization of the tablet upstream from the target sites makes an immediate release of a high concentration of the active ingredient(s) contained in the active phase in order to rapidly saturate the target sites, followed by a prolonged release of a smaller quantity of the active ingredient(s) in order to maintain the state of saturation of the target site for a long period of time, particularly advantageous.

In addition, a release of the totality of the quantity of the active ingredient(s) upstream from the target sites practically excludes or at the very least very considerably reduces a deviation from the metabolic pathways which is observed with non-floating tablets. With these latter, a significant quantity of the active ingredient(s) is released downstream from the target sites, said active ingredient(s) being then converted by metabolic routes different from the metabolic routes initially targeted.

The active ingredients which may be included in a pharmaceutical composition according to the invention are for example flutamide or metformin.

In addition, use will advantageously be made of one or more active ingredients capable of ionizing principally in the gastro-intestinal tract as well as of active principles which because they are released very slowly, can not saturate the target enzymatic sites when they are formulated with conventional pharmaceutical compositions.

In accordance with another feature, use will be made of one or more active ingredients having a local action on the digestive mucosa. The anti-acids, like for example magnesium hydroxide which are used in a high dosage form, belong to this class of active ingredients.

More generally, a pharmaceutical composition according to the invention contains one or more active ingredients selected from the following active ingredients:

antibiotics: cephalosporins (cefacior)
    anti-emetics: metoclopramide
    anticonvulsants: valproic acid and its derivatives, carbamazepine
    antivirals: nucleosides (acyclovir),
    calcium inhibitors: nicardipine and its derivatives, virapamil
    diuretics: sulfamides (furosemide)
    antiarrhythmics: dihydroquidine
    mineral supplements: potassium
    antidiabetics: biguanidine (metformin and its derivatives)
    anti-inflammatories: etodolac, ketoprofen, ibuprofen
    antihormones: antiandrogens (flutamide)
    antiparkinsonian agents: levodopa/carbidopa
    beta blockers: acebutolol
    neuroleptics: butyrophenones (penfluridol), phenothiazines.

According to the invention, the active phase contains a high dosage of active ingredient(s).

Preferably, the active phase contains an amount of active ingredient of at least about 80%, preferably at least 85% and even more preferably at least about 90% by weight of the active phase.

In accordance with this particular embodiment, the pharmaceutical composition according to the invention is in addition characterized in that the active phase is constituted by a composition containing at least one active ingredient and, as disintegrating agents, hydroxypropylmethylcellulose, highly substituted hydroxypropylcellulose and/or ethylcellulose in quantities less than 15% by weight of the active phase and in a form making it possible to obtain a disintegrating effect while preventing the formation of a continuous network. For purposes of the invention, highly substituted hydroxypropylcellulose should be understood to refer to any cellulose comprising a minimum of 50%, preferably a minimum of 65%, and more preferably a minimum of 75% substitution by hydroxypropoxy groups.

The constitution of an active phase such as defined above is described in detail in the French patent application No. 97 10 560 filed on 21 Aug. 1997, the content of which is incorporated here by reference.

The invention also relates to a tablet constituted, at least in part, by a floating pharmaceutical composition such as defined above.

In general, such a tablet may consist of a double core tablet or also a multilayered tablet.

In accordance with a first feature, a tablet according to the invention is characterized in that it is a bilayer composite constituted of a first layer of active phase and a second layer of inactive phase.

According to a first embodiment, the first and second layers have a common contact surface.

According to a second embodiment, the active phase and the inactive phase are separated by a polymer layer.

In accordance with a second feature, a tablet according to the invention is characterized in that it is a triple layer tablet constituted of a layer of active phase sandwiched between a first and a second layer of inactive phase.

The active phase may be separated from the first and second inactive phase by a polymer film.

In accordance with a third feature, a tablet according to the invention consists of a triple layer tablet constituted of a layer of inactive phase sandwiched between a first and a second layer of active phase.

In accordance with a fourth feature, a tablet according to the invention is available in the form of micro-granules.

According to another embodiment of a tablet according to the invention, the latter is constituted of an internal core of active phase and an external layer of inactive phase coating the internal core (double-cored tablet).

In such an embodiment, the internal core of active phase may be separated from the external layer of inactive phase by a polymer film, so as to prevent direct contact between the active phase and the inactive phase and, consequently, an interaction between the excipients of the inactive phase and the active ingredients contained in the active phase.

In accordance also with another embodiment, the active phase may itself be constituted of an internal core and an external phase:

a) the internal core being constituted of a composition comprising at least one active ingredient and, as disintegrating agents, hydroxypropylmethylcellulose, highly substituted hydroxypropylcellulose and/or ethylcellulose in quantities less than 15% by weight of the active phase and in a form making it possible to obtain a disintegrating effect while preventing the formation of a continuous network;

b) the external phase comprising at least one compound with a high disintegrating effect and an efficacious quantity of the active ingredient(s) contained in the internal core.

The external phase comprises at least an efficacious quantity of one or more active ingredients and at least one compound with a high disintegrating effect.

Such an embodiment of the present invention is particularly advantageous because it permits the rapid release of a high dose of active ingredient by dissolution of the external phase, then the delayed release of the active ingredient(s) contained in the internal core.

Such a pharmaceutical form will be advantageously made use of, for example, in the case of the anti-acid active ingredients described previously or any other active ingredient requiring a multimodal release, for example bimodal, which is characterized by a rapid release followed by slow release of the active ingredient.

In this particular embodiment of a tablet according to the invention, the inactive phase is added on to the external surface of the double core, for example by compression.

In yet another particular embodiment of a tablet according to the invention, this tablet is suitable for the release of the active ingredient at the post-gastric level, for example in the intestinal tract and in the jejunum.

In accordance with a first feature, such a tablet comprises in addition to the active phase and the inactive phase such as previously described, a polymer possessing muco-adhesive properties. In a very preferred manner, the polymer possessing muco-adhesive properties coats the external surface of the inactive layer. This particular embodiment of a tablet according to the invention confers on the tablet adhesive properties to the mucosa while maintaining precise control of the release of the active ingredients contained in the active phase.

According to this embodiment, such a tablet adheres to the mucosa, preferably the post-gastric mucosa through the outside of the inactive phase whereas the active ingredient is released from the active phase which is directly in contact with the external aqueous medium. In the case of a triple layer composite constituted by one layer of active phase sandwiched between a first and a second layer of inactive phase, each of the external surfaces of the layers of inactive phase is coated with a polymer possessing muco-adhesive properties.

According to this particular embodiment of a tablet according to the invention, release of the active ingredient is obtained by erosion and diffusion from the active layer, without simultaneous erosion of the inactive layer coated with a polymer which adheres to the mucosa.

When the tablet is available in the form of micro-granules, each of the micro-granules is then coated with a polymer possessing muco-adhesive properties.

Preferably, the polymer possessing muco-adhesive properties is selected from the cellulose and their derivatives, carbomer (carbopol) and its derivatives, povidone and its derivatives or also polyvinylacetate (PVA) and its derivatives.

In accordance with a second feature, a tablet according to the invention may be rendered gastro-resistant when the active ingredient(s) contained in the active phase must be released downstream from the stomach, at the post-gastric level as, for example, at the level of the intestine or jejunum.

In accordance with this particular feature of a tablet according to the invention, the tablet is coated with a layer of a gastro-resistant polymer capable of being dissolved at a pH higher than the pH of the stomach, i.e. at a pH higher than 4, and much more preferably at a pH higher than 2.

When the tablet is available in the form of micro-granules, each of the micro-granules is coated with a layer of a gastro-resistant polymer.

Preferably, the gastro-resistant polymer is selected from cellulose acetate phthalate, hydropropylmethylcellulose phthalate (also called hypromellose phthalate) or also a methacrylic acid copolymer.

In a much preferred embodiment of a gastro-resistant tablet according to the invention, such a tablet will comprise in combination both a polymer possessing muco-adhesive properties and a gastro-resistant polymer, in conformity with the embodiment described above.

A gastro-resistant tablet according to the invention is particularly suited to the release of active ingredients whose release window is sensitive to an acid pH and which can consequently be degraded by the acidic pH of the gastric juice.

A gastro-resistant tablet according to the invention is consequently particularly suitable when the release of an active ingredient is desired whose target sites are localized in the intestine.

In accordance with yet another feature, a gastro-resistant tablet according to the invention is particularly advantageous in all cases where the release of the active ingredient(s) is desired at the post-gastric level.

A gastro-resistant tablet according to the invention will preferably comprise one or more active ingredients selected from the following active ingredients:

Acyclovir and its salts
Ranitidine and its salts
Alfusozine and its salts
Metformin and its salts
Nicardipine and its salts
Antibiotics and more particularly the β-lactamins and in particular CEFACLOR and its salts or also ciprofloxacin
Hormones and more particularly the estrogens and progestational hormones such as for example estradiol and progesterone;
Methyldopa and its salts
Levodopa
Inosine
Verapamil
Nifedipine
Tribavidin
Zidovudine
Ketanserin
Loperamide
Cimetidine
Misoprostol
Omeprazole Another subject of the invention is a process for the preparation of a tablet such as defined above, characterized in that at least one layer of active phase and at least one layer of inactive phase are placed in contact, then cemented by compression.

In accordance with yet another feature, the active phase may be constituted of micro-granules containing a combination of the active ingredient(s) with the excipients. The corresponding tablet is then constituted by a core of active phase comprising said micro-granules surrounded by an external layer constituted by the inactive phase. If necessary, the internal core of active phase and the external layer of inactive phase are separated by a polymer film according to procedures well-known to the specialist.

A gastro-resistant tablet according to the invention is manufactured preferably by procedures making use of a fluidized air bed, a film-forming turbine or also a mixing-granulation-drying (MGD) procedure well-known to the specialist.

In general, the specialist can determine for each active ingredient the quantities of excipients which are sufficient, in particular by using the dissolution tests described in the "European Pharmacopoeia" (1997, Method of Pharmacotechniques, pages 127 to 130). These tests are performed by placing the pharmaceutical form containing the active ingredient in an apparatus with paddles, with baskets, or continuous flow and by observing the kinetics of release of the active ingredient.

The one skilled in the art can thus determine in a simple and reliable manner the active ingredient(s)/excipient(s) ratios and modulate the release (immediate or delayed) as a function of therapeutic needs.

The invention is also illustrated by the figures and the following examples, without being limited by them:

FIG. 1 illustrates several embodiments of a floating tablet according to the invention:
A: tablet constituted by an internal core of active phase and an external layer of inactive phase.
B: triple layer tablet constituted by a layer of active phase sandwiched between two layers of inactive phase.
C: bilayer tablet constituted by a layer of active phase and a layer of inactive phase.

Figure 2:
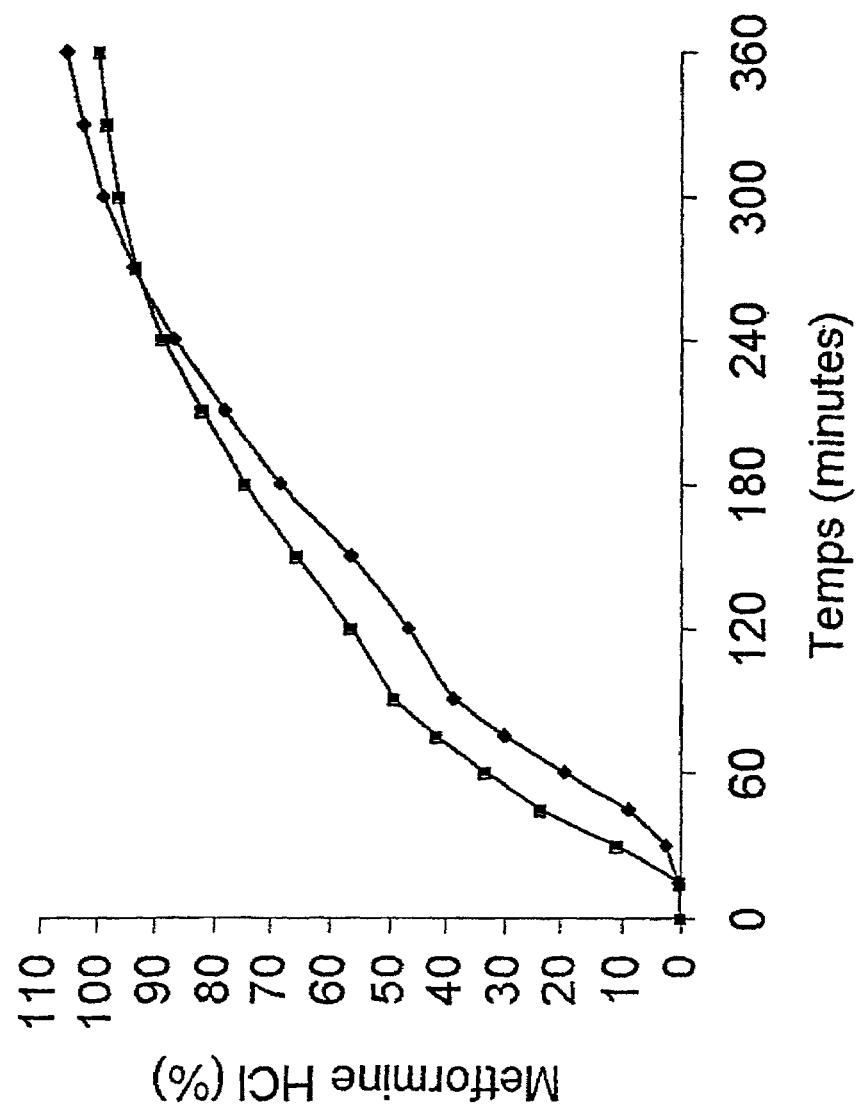

FIG. 2 illustrates the comparative results of the dissolution profile of a bilayer floating tablet according to the invention, and a tablet constituted uniquely of a layer of active phase.

Along the abscissa, percentage of active ingredient metformin released

Along the ordinate, time elapsed after contact of the tablets with an aqueous medium.

The squares represent the results obtained with the active phase of the tablet described in Example 1.
The lozenges represent the results obtained with the tablet of Example 1.

EXAMPLE 1

Programmed Release Tablet Containing Metformin Hydrochloride

| Name of the constituents | Quantity (in %) |
|---|---|
| Active layer | |
| Metformin HCl | 51.33 |
| Carbomer (Carbopol ®974) | 3.02 |
| Highly substituted hydroxypropylcellulose (Klucel ® HXF) | 4.53 |
| Magnesium stearate | 0.06 |
| Inactive layer | |
| Hydroxypropylmethylcellulose (Metolose ® 90SH4000SR) | 24.64 |
| | 9.20 |

-continued

| Name of the constituents | Quantity (in %) |
|---|---|
| Anhydrous monosodium citrate Sodium bicarbonate (13/50) | 7.23 |

Composition available in the form of triple layer or bilayer tablets.

Method of preparation:
a) Active layer: wet granulation approach
Introduce metformin hydrochloride and CARBOPOL® into a mixer granulator of the ROTOLAB® type or equivalent
Mix with the aid of a triple blade stirrer for 3 minutes.
Start the wetting operation by incorporating purified water as wetting solution.
Granulate the whole until a satisfactory grain quality is obtained.
Dry the grain
Calibrate the grain on an oscillating granulator ERWEKA AR 401 or equivalent.
Mix first hydroxypropylcellulose, then magnesium stearate with the calibrated grain in a suitable mixer.
b) Inactive layer
A homogeneous mixture of the different constituents of this layer is prepared.

The two compositions a) and b) thus prepared serve to feed the tabletting machine equipped with format 13.5R17 punches.

The tablets obtained from this manufacture are either bilayer or triple layer of 974 mg mean mass per unit.

EXAMPLE 2

Programmed Release Tablets Containing Flutamide

| Name of the constituents | Quantity (in %) |
|---|---|
| Active layer | |
| Flutamide | 70.00 |
| Povidone K90F | 2.00 |
| Hydroxypropylmethylcellulose (Metolose ® 90SH4000SR)) | 1.00 |
| | 6.25 |
| Magnesium stearate | 0.25 |
| Inactive layer | |
| Hydroxypropylmethylcellulose (Metolose ® 90SH100000SR) | 20 |
| Potassium bicarbonate | 6.75 |

In this case, the active layer is produced by a wet granulation procedure and tabletted on a 12 mm diameter punch.

The inactive layer serves to feed a tabletting machine for the purpose of producing double core tablets.

EXAMPLE 3

Study of the Dissolution Profile of a Pharmaceutical Composition According to the Invention Compared with the Dissolution Profile of a Conventional Pharmaceutical Composition The dissolution profiles of two pharmaceutical compositions were studied respectively for:

a tablet of a pharmaceutical composition according to the invention, in conformity with Example 1;

a tablet containing only the active phase of a pharmaceutical composition in conformity with Example 1.

The tablets of each of the above pharmaceutical compositions were immersed in a buffer medium adjusted to pH 6.8 in a paddle stirrer for conventional dissolution analysis, the speed of the paddles being fixed at 100 revs./minute and the volume of medium being 1000 ml at a temperature of 37° C.

The tablets tested are tablets obtained according to a 13.5R17 compression format. During the test, the tablets are "ballasted", i.e. placed in a JAGO type basket, itself deposited at the bottom of the dissolution tank.

The results are reported in FIG. 2.

As can be seen, the dissolution profiles of the active ingredient metformin hydrochloride are identical in the case of the two tablets tested.

These results show that the addition of the constitutive inactive phase of a tablet according to the invention is without observable effect on the dissolution profile of the ingredient contained in the active phase.

EXAMPLE 4

Study of the Duration and Flotation of a Tablet Constituted of a Pharmaceutical Composition According to the Invention The tablet tested is a triple layer tablet such as described in FIG. 1B, prepared essentially as described in Example 1.

The layer of active phase is tabletted between two layer of inactive phase of the same composition.

The inactive phase comprises a monosodium citrate/sodium bicarbonate ratio equal to 65/35. The resistance to rupture of the tablets is about 390 Newtons.

The tablets were immersed in respectively:

100 ml of water. R conforms to the section "Reagents" of the Pharmacopoeia at a temperature of 37° C.

100 ml of 0.1N HCl at 37° C.

In the water R at 37° C., the latent period before flotation of the tablets is 47. This latent period is 29 seconds in 100 ml of 0.1N HCl. In the two aqueous media the tablets float after more than 16 hours.

The invention claimed is:

1. A tablet floating pharmaceutical composition comprising:
   a) a first phase, termed active phase, consisting of a composition comprising at least one active ingredient and a disintegrating agent comprising highly substituted hydroxypropylcellulose that is at least 50% substituted, provided in an amount of less than 15% by weight of the active phase and in a form to obtain a disintegrating effect while preventing the formation of a continuous network;
   b) a second phase, termed inactive phase, comprising at least one gas-generating system and at least one hydrophilic polymer or a porous mineral compound, the active phase comprising a quantity of active ingredient(s) constituting at least 80% by weight of the active phase.

2. The tablet according to claim 1, wherein the hydrophilic polymer of the inactive phase is selected from polysaccharide substances and protein substances.

3. The tablet according to claim 2, wherein the polysaccharide substances and related substances are selected from the group consisting of galactomannans, galactomannans derivatives, starch, starch derivatives, gum arabic, tragacanth gum, pectins, pectin derivatives, alginates, cellulose, cellulose derivatives, high molecular weight dextrans, xanthan, and xanthan derivativese.

4. The tablet according to claim 2, wherein the protein substances are selected from gelatin and purified derivatives thereof.

5. The tablet according to claim 1, wherein the hydrophilic polymer of the inactive phase is selected from the group consisting of poloxamers, high molecular weight polyethylene glycols, polymers of methacrylic acids, polymers of acrylic acids, derivatives of methacrylic acid, and derivatives of acrylic acid.

6. The tablet according to claim 1, wherein the porous mineral compound of the inactive phase is selected from the group consisting of silicas and silica derivatives.

7. The tablet according to one of claims 1 to 6, wherein the gas-generating system of the inactive phase is a carbon dioxide generating system.

8. The tablet according to claim 7, wherein the carbon dioxide generating system comprises an alkali or alkaline earth metal carbonate or bicarbonate.

9. The tablet according to claim 8, wherein the alkali or alkaline earth metal carbonate or bicarbonate is in combination with an acid selected from the group consisting of a mono-carboxylic acid, a poly-carboxylic acid and a partial salt of a polycarboxylic acid.

10. The tablet according to one of claims 1 to 6, wherein the hydrophilic polymer or the porous mineral compound comprises from 10% to 70% by weight of the inactive phase.

11. The tablet according to one of claims 1 to 6, wherein the gas-generating system comprises from 5% to 60% by weight of the inactive phase.

12. The composition according to claim 1, wherein the at least one active ingredient is present in ionic form in an acidic medium and is degraded by acidic pH.

13. The tablet according to claim 1, wherein the tablet is a bilayer composite comprising a first layer of the active phase and a second layer of the inactive phase.

14. The tablet according to claim 1, wherein the tablet is a triple layer comprising a layer of the active phase placed between two layers of the inactive phase.

15. The tablet according to claim 1, wherein the tablet is a triple layer comprising a layer of the inactive phase placed between two layers of the active phase.

16. The tablet according to claim 1, wherein the tablet comprises an internal core of the active phase and an external layer of the inactive phase coating the internal core.

17. The tablet according to claim 1, wherein the tablet comprises micro-granules.

18. The tablet according to claim 1, wherein the active phase is a double core comprising an internal core and an external phase, wherein:
   a) the internal core comprises at least one active ingredient and, as disintegrating agents, highly substituted hydroxypropylcellulose that is at least 50% substituted, in quantities less than 15% by weight of the active phase, wherein the core disintegrates while preventing the formation of a continuous network; and
   b) the external phase comprising at least one compound with a high disintegrating effect and an efficacious quantity of the active ingredient.

* * * * *